(12) United States Patent
Schrier et al.

(10) Patent No.: US 6,270,770 B1
(45) Date of Patent: *Aug. 7, 2001

(54) CHICKEN ANAEMIA AGENT BROILER VACCINE

(75) Inventors: Carla Christina Schrier, Boxmeer; Pieter Matthijs Van Dijk, Blitterwijck, both of (NL)

(73) Assignee: Akzo Nobel N.V., Arnhem (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/860,523

(22) PCT Filed: Jan. 4, 1996

(86) PCT No.: PCT/EP96/00122

§ 371 Date: Oct. 24, 1997

§ 102(e) Date: Oct. 24, 1997

(87) PCT Pub. No.: WO96/20727

PCT Pub. Date: Jul. 11, 1996

(30) Foreign Application Priority Data

Jan. 6, 1995 (EP) .................................................. 95200018

(51) Int. Cl.⁷ ........................... A61K 39/00; A61K 39/38; A61K 39/325; A61K 39/12

(52) U.S. Cl. ..................................... 424/184.1; 424/201.1; 424/202.1; 424/204.1; 424/816; 435/235; 435/236; 435/237; 435/238; 435/239

(58) Field of Search .............................. 424/184.1, 201.1, 424/202.1, 204.1, 816; 435/235, 236, 237, 238, 239

(56) References Cited

U.S. PATENT DOCUMENTS 5,686,077 * 11/1997 Schrier ............................... 424/201.1

FOREIGN PATENT DOCUMENTS

| 0483911 | 5/1992 | (EP) . |
| 0533294 | 3/1993 | (EP) . |
| 0 533 294 A1 * | 3/1993 | (EP) ............................... A61K/39/12 |

OTHER PUBLICATIONS

M.S. McNulty et al., *Avian Diseases*, 35:263–268, 1991.

* cited by examiner

*Primary Examiner*—Jeffrey Stucker
*Assistant Examiner*—Brett Nelson
(74) *Attorney, Agent, or Firm*—William M. Blackstone

(57) ABSTRACT

The present invention for the first time discloses a health problem in broilers at about 3–5 weeks, resulting in significant production losses, and demonstrates that these production losses can be prevented by a live attenuated CAA vaccine for mucosal administration.

8 Claims, No Drawings

CHICKEN ANAEMIA AGENT BROILER VACCINE

This application is a 371 of PCT/EP96/00122 filed Jan. 6, 1996.

The present invention is concerned with a live attenuated CAA vaccine.

Chicken anaemia agent (CAA) is the causative agent of a disease known as avian infectious anaemia, anaemia dermatitis syndrome or blue-wing disease and was first described by Yuasa et al. in 1979 (Avian Diseases 23, 366–385, 1979).

Most outbreaks of naturally occurring CAA-induced disease have been reported in broilers. The disease is acute and the first signs usually occur at 10–14 days of age. This clinical disease is characterized by a sudden increase in mortality, usually around 5–10%, but up to 60% has been reported. Peak mortality occurs within 5 to 6 days of onset of disease. Further clinical signs include depression and anorexia. Moreover, severe anaemia, hemorrhages throughout the body, atrophy of the thymus and bursa of Fabricius and yellowish bone marrow is seen in affected chickens McNulty, M. S., Avian Pathol. 20, 187–203, 1991).

The clinical syndrome in broilers occurs in commercial flocks when in-lay breeders with no previous exposure to the virus, i.e. seronegative breeders, become infected. CAA is transmitted vertically to the progeny, which develop the disease at 10 to 14 days. No clinical signs have been reported in the infected breeders, and there is no apparent effect on egg production, hatchability or fertility, because chicks develop an age resistance to CAA-induced disease.

The anaemia dermatitis syndrome in chickens caused by the vertical spread of CAA from the breeder through the egg to the progeny can be prevented by ensuring that the parent flocks develop antibodies to CAA before the onset of lay. This can occur through natural exposure of the flocks to the virus. However, due to the significant economical losses resulting from clinical CAA it is preferable to vaccinate the parent stock in order to induce a sero-conversion in breeder flocks during the rearing period. Older birds inoculated with the virus develop significant titers of neutralising antibodies at about 3 weeks after infection. These virus neutralizing antibodies are passed from the breeder to the progeny via the egg such that the chickens obtain a titer of maternal antibody which protects the young chickens against CAA infection during the first weeks after hatching.

Yuasa, N. et al. (Avian Diseases 24, 197–201, 1980) disclose that commercial chickens are generally refractory to CAA field infection and that this was closely related to the presence of maternal antibodies in the chick. Otaki, Y. et al. (Avian Pathology 21, 147–151, 1992) showed that even a very low level of maternal antibody is effective for preventing CAA-infection. Maternal antibodies could be detected up to 3 to 5 weeks of age. In a study using chickens with maternal derived antibodies (MDA) against CAA Yuasa, N. (Poultry Diseases, Proc. 2nd Asian/Pacific Poultry Health Conference, 385–406, 1988) has shown that the antibody-positive rate starts decreasing at about 3 weeks of age.

Vielitz et al. (J. Vet. Medicine 34, 553–557, 1987) describes a CAA vaccine comprising the not-attenuated Cux-1 anaemia pathogen suitable for vaccinating parent stock at the age of 13–15 weeks. Although chickens vaccinated intramuscularly with this vaccine developed antibodies 2 weeks after vaccination, in chickens vaccinated via drinking water antibodies were observed only from 4 weeks after administration of the vaccine.

Recently, the first live attenuated vaccine for administration to older birds has been disclosed in European patent application No. 0533294 (Akzo Nobel N. V.). Although this vaccine was able to elicit a sufficient amount of CAA neutralizing antibodies in these birds when administered parentally, vaccination with the live attenuated vaccine via the drinking water or spray route did not induce an adequate immune response (Steenhuisen, W. et al., International symposium on infectious bursal disease and chicken infectious anaemia, Rauischholzhausen, Germany, 1994).

In addition to the vertically spreading of CAA in chickens the virus also spreads horizontally. Horizontal spread in broilers probably occurs through ingestion of faecally contaminated material or contaminated fomites. Horizontal acquired infections in broiler progeny of immune breeder flocks also occur when MDA against CAA are declining. However, the effect of horizontal CAA infection in broilers is not clear.

McNulty et al. (Avian Diseases 35, 263–268, 1991) compared production and performance parameters of clinically normal broiler flocks which had antibody to CAA at slaughter with clinically normal broiler flocks which had no antibody to CAA at slaughter and reported that subclinical CAA in broilers of about 6 weeks of age was associated with significant economic losses. It was suggested to devise a live attenuated vaccine for broilers to decrease the losses associated with subclinical CAA. Contrary to this Goodwin, M. A. et al. (Avian Diseases 37, 542–545, 1993) found no differences in weight gain or production performance among healthy CAA-antibody positive and negative SPF chicks and broiler chicks.

The existence of a new type of health problems in broilers and its solution is for the first time disclosed herein. This type of problem can be observed in broilers from about 3 weeks of age and is characterized by the following symptoms:

an arrest of growth during the third or fourth week of age a decrease of the feed-conversion increased leg problems and lameness slight increase of mortality towards the end of the growing period pale appearance undigested feed in the feaces. These problems resulted in successive production rounds with disappointing performance results in broiler farms with previous good performance records.

An object of the present invention is to provide a vaccine which is able to prevent this performance drop syndrome affecting broiler flocks during the growth period, taking into account that the vaccine must have a beneficial effect in the face of maternal antibodies.

A further object of the present invention is to provide a vaccine which is able to induce a beneficial response within a very short time after administration in order to prevent the early performance drop in broilers.

The present invention provides a vaccine for mucosal administration for the protection of broilers against production drop and comprising a live attenuated CAA virus and a pharmaceutically acceptable carrier.

It is surprising, that a live attenuated CAA vaccine for mucosal administration is able to stimulate the broiler's immune system within a very short time after administration, which is a prerequisite for an effective prevention of the production drop syndrome which affects the broilers already from about 3 weeks of age, because a CAA vaccine for parent stock derived from a virulent CAA, administered via the mucosal route, i.e. via drinking water developed an immune response only from 4 weeks onwards after administration (Vielitz et al., supra). In addition, with respect to the live attenuated CAA vaccine disclosed in EPA 0533294, it was demonstrated that such a vaccine in a form suitable for spray or drinking water administration did not induce an adequate immune response (Steenhuisen, W. et al., supra) in older birds.

The term broiler refers to a young, tender chicken, specially produced for the table. These fast growing chicks specially reared for the slaughter are the progeny of special types (heavy) breeder hens and cocks. For example, female broiler breeders are usually derived of the White Plymouth Rock-Sussex or New Hampshire breeds. Broiler breeder males are usually derived from the Cornish breed, such as Cornish Indian game.

The vaccine according to the present invention is in a form suitable for mucosal administration. This means that the vaccine is administered such that it is brought into contact with the broiler's mucosal membranes, for example of the respiratory tract, intestinal tract or the eye. Therefore, the vaccine can be applied intranasally, orally, intraocularly or intracloacal.

In a preferred embodiment of the invention the vaccine for intranasal or oral administration is in a form suitable for administration by spray, including aerosol, or drinking water, respectively.

The spray or aerosol method involves the administration of the live attenuated CAA virus vaccine incorporated in small liquid particles. In the former method particles usually have an initial droplet size ranging from 10 to 100 microns and in the latter method from <1 to 50 microns.

In order to prevent inactivation of the live vaccine virus because of increased concentration of dissolved salts as a result of desiccation of the (tap) water particles, small amounts of a protein protectant, such as skimmed milk, skimmed milk powder or gelatin can be added to aqueous phase.

In the spray or aerosol administration, generally a known amount of the virus is discharged into a fixed air space rather than being administered directly to each broiler. Typically, for 20 broilers occupying 1 m² of floor space, the average volume of air is about 0.14 m³ or less per bird, depending upon the height of the ceiling. However, this type of administration is also possible in houses with open sides. In closed houses with mechanical ventilation, the ventilation is usually switched off for a short period (e.g. 20 minutes). In such a case, vaccination is preferably carried out during periods when air conditions are calm, in order to prevent the generated droplets to diffuse rapidly out of the building.

For the generation of the small particles, conventional spray-apparatus and aerosol generators can be used. Also the drinking water vaccination can be carried out using a conventional apparatus. Details concerning conventional spray/aerosol—and drinking water vaccination can be found in the "Compendium, administration of poultry vaccins" issued by the Gezondheidsdienst voor Pluimvee, Doorn, the Netherlands, van Eck et al., VI–VII, 1988.

In the administration by the drinking water route it is customary to deprive the broilers of water for about 2 to 4 hours before placing the vaccine containing water in front of them, and it is important that there is enough drinker space for all birds to drink evenly.

In order to prevent a dramatic reduction of the viable vaccine virus by the presence of small amounts of chlorine, iron, zinc or copper ions in the drinking water, preferably a protectant such as skim milk (powder) is added to the water containing vaccine.

The vaccine is diluted according to the age of the broilers so that an adequate amount of vaccine is allowed. The quantity of water generally required per bird for the drinking water vaccination is about 10–15 ml for 10 to 14 day old broilers and 20–30 ml for 3 to 8 weeks old broilers.

Live attenuated CAA to be used in the vaccine according to the invention are known in the art. For example, Bülow von, V. and Fuchs, B. (J. Vet. Med. 33, 568–573, 1986) demonstrated that the pathogenicity of CAA strain Cux-1 was decreased after 12 serial passages in MDCC-MSB1 cells.

Preferably, the vaccine according to the invention is derived from CAA which have been attenuated by serial passages of a virulent parental strain in embryonated eggs. Such CAA have the characteristic that they induce lesions in chicken embryo's but display a reduced pathogenicity for young chicks, in particular for one-day-old chicks (European patent application No. 0533294).

A vaccine according to the invention can be prepared from any CAA strain available or obtainable from chickens suffering from infection with this pathogen. A number of CAA isolates have been described already in the prior art, e.g. the Cux-1 strain, the Gifu-1 strain, the TK-5803 strain, the CAA82-2 strain and strain 26P4 (CNCM accession No. I-1141).

The method for the preparation of the vaccine according to the present invention is conventionally and may include the steps of inoculating a susceptible substrate with attenuated CAA, in particular with such CAA which have been attenuated in embryonated eggs, propagating the CAA and harvesting CAA containing material.

Preferably, the substrate on which CAA is propagated are SPF embryonated eggs. Embryonated eggs can be inoculated with for example 0.2 ml CAA containing suspension or homogenate comprising at least $10^{3.0}$ TCID$_{50}$ per egg. Preferably, eggs are inoculated with at least $10^{4.5}$ TCID$_{50}$ and subsequently incubated at 100° F. for 13 days. After 13 days the CAA product can be harvested by collecting the embryo's and/or the membranes and/or the allantoic fluid and appropriate homogenizing this material. The homogenate can be centrifuged thereafter for 10 min. at 2500 g followed by filtering the supernatant through a filter (100 μm).

Alternatively, the attenuated CAA can be inoculated onto a susceptible cell culture, e.g. MDCC-MSB1 cells, followed by cultivation of the cells and collecting the propagated virus.

Harvestable virus titres, preferably of at least about $10^{6.0}$ TCID$_{50}$/ml as assayed in MDCC-MSB1 cells can be obtained after 10–18 days post-inoculation, preferably 13 days after inoculation of embryonated eggs.

The harvested fluids or virus material can be combined with a pharmaceutically acceptable carrier or diluent as described below for final product filling and/or frozen in bulk or freeze-dried.

The vaccine according to the invention comprises an effective dosage of the live attenuated CAA, i.e. an amount of immunizing CAA that will induce immunity in broilers against pathogen associated performance drop. Immunity is defined herein as the induction of a significant higher level performance results in broilers in a flock after vaccination compared to an unvaccinated flock.

A vaccine according to the invention generally may comprise $10^{2.0}$–$10^{6.0}$ TCID$_{50}$ of the live attenuated CAA per field dose for each broiler, preferably $10^{4.0}$–$10^{5.0}$ TCID$_{50}$ of the virus per field dose for each broiler.

The vaccine according to the invention containing the live virus can be prepared and marketed in the form of a suspension or in a lyophilized form and additionally contains a pharmaceutically acceptable carrier or diluent customary used for such compositions. Carriers include stabilizers, preservatives and buffers. Suitable stabilizers are, for example SPGA, carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline) alcohols and polyols (such as glycerol).

As the newly observed health problems in broilers resulting in a performance drop emerges in the broilers from about 3–5 weeks of age, the vaccine should be administered to the broilers before or during the onset of the disease.

Preferably, the vaccine is administered to the broilers during the first 4 weeks after hatch. In particular, the vaccine according to the invention is effective if it is administered to broilers which are maternally immune, i.e. contain detectable levels (VN or Elisa titers $\geq 1:32$) of maternally derived antibodies (MDA) in their serum. It is demonstrated herein that surprisingly the vaccine according to the invention is able to induce a beneficial effect in the face of MDA and to raise a quick immune response such that immunity is achieved before the onset of the newly described health problems in broilers (3–5 weeks after hatch).

EXAMPLE

Material and Methods
  20 potential trial farms were identified by the local practitioner in cooperation with the Regional Animal Health Service.
  The broiler farm belonged to two different integrations.
  The flocks sizes varied from 16,000 to 88,000 birds per round.
  Approximately 700,000 birds were vaccinated, whereas approx. 260,000 were left unvaccinated.
  Various breeds were involved.
Vaccines/Vaccination-scheme
  Participating flocks were vaccinated according to the following scheme:
  Day old: ¼ dose ND Vaccine Nobilis Clone-30®, hatchery coarse spray.
  Approx. 16 days: CAA, drinking water or spray.
  Approx. 19 days: Gumboro Vaccine Nobilis D78®, drinking water, full dose.
  Approx. 21 days: IB+ND Vaccine Nobilis Ma5 Clone-30®, coarse spray, full dose.
  For aerosol CAA broiler vaccination per 10.000 doses (about $10^{5.0}$ TCID$_{50}$/animal), 1 liter water is used for reconstitution. The CAA vaccine is derived from the attenuated 19th egg-passaged 26P4 strain (European patent application No. 0533294). By means of an automizer (Atomist) an aerosol cloud is blown over the heads of the broiler chicks. By shutting down the ventilation (for 30 min.) the vaccine cloud is prevented from leaving the house. For the drinking water administration, a pre-solution of the required amount of the vaccine virus (1.000 doses per 1000 chicks, about $10^{5.0}$ TCID$_{50}$/animal) mentioned-above in cold tap-water is prepared first. This solution was subsequently added to the central drinking water supply, containing that amount of water the group of broilers can consume within about 2 hours. After thirsting the broilers for about 2 hours the birds are admitted to the central drinking nipple system. Of the first seven flocks vaccinated, 9 houses were vaccinated by Atomist (aerosol) and four houses were vaccinated by drinking water. As it was clear then that there was no difference in effects between the administration by Atomist and by the drinking water method, all subsequent vaccinated flocks were vaccinated by the aerosol method. On 11 production rounds, some houses were left unvaccinated with CAA, as negative controls.

Parameters Used
  Flocks were observed clinically for vaccination reaction.
  Blood samples were taken at age of vaccination and at slaughter age, for serology.
  Production data were collected through the integrations.
  Production data were compared with production data of the previous 5 rounds.
  Where possible, production data of vaccinated houses were compared with data of unvaccinated controls.

RESULTS

Vaccination Reaction
  In none of the 20 flocks any adverse reaction was noticed. The mortality figures do not suggest any negative effect either, on the contrary (see "mortality"). There is a tendency towards lower mortality in the vaccinated flocks, which is strongest in the post vaccination mortality.

Serological Response
  CAA-titers at time of vaccination (approx. 2 weeks of age): On 4 out of 20 farms titers were below 4.5. On 16 out of 20 farms titers were above 5.0 (maternal immunity).
  Of 16 farms CAA-titers at slaughter age are available (approx. 6 weeks): On 3 out of 16 farms titers were found above 5.0. On 13 out of 16 farms no titers above 4.0 were found, as serological indication of either field infection or seroconversion after vaccination. This means that the vaccination has taken, without inducing seroconversion before slaughter age. If it is assumed that CAA was present on the farms and causing problems, it means that the vaccine has prevented the field virus from inducing seroconversion. The seroconversion in some of the flocks may have been caused by CAA-field infection before the day of vaccination.

Production Data
  Production index: The production index (PI) is calculated from the formula (Voeten and Brus):

$$PI = \frac{\% \text{ surviving birds} \times \text{kg growth/day/chicken} \times 100}{\text{feed conversion}}$$

The formula takes in account mortality, growth and feed conversion, and can be used to make comparisons between technical performances of different flocks at different times.
Results are shown in table 1.

TABLE 1

| | PI vaccinated | PI previously (1 round) | PI previously (5 rounds) |
|---|---|---|---|
| Average 20 farms | 239 | 212 | 216 |

The average PI of the 20 CAA-vaccinated broiler flocks was 239.
The average PI of the last previous non-vaccinated rounds on those 20 flocks was 212, so there was an average improvement of 27 points.
The average PI of the previous 5 unvaccinated rounds on those farms averaged over the 20 flocks, was 216, so compared with that, the vaccinates scored 23 points better.

Of 16 out of the 20 flocks, the PI was the best performance, compared to the 5 previous unvaccinated rounds.

Feed Conversion (FC)

Results are shown in table 2.

TABLE 2

|  | FC 1500 g vaccinated | FC 1500 g previously (1 round) | FC 1500 g previously (5 rounds) |
| --- | --- | --- | --- |
| Average 20 farms | 1.66 | 1.81 | 1.70 |

The average FC (at a weight of the chicken of 1500 g) of the 20 flocks was 1.66.

The average FC of the last unvaccinated previous rounds on those farms was 1.81. So there had been an average improvement of 0.15.

The average FC of the previous 5 unvaccinated rounds, averaged over the 20 flocks, was 1.79. Compared to that figure, the trial rounds score 0.13 points better.

Of 16 out of the 20 flocks, this was the best performance, compared to the 5 previous unvaccinated rounds.

Growth Per Day

Results are shown in table 3.

TABLE 3

|  | growth/day vaccinated | growth/day previously (1 round) | growth/day previously (5 rounds) |
| --- | --- | --- | --- |
| Average 20 farms | 44.6 | 42.8 | 42.8 |

16 out of 20 flocks have a higher growth per day, 4 have a lower growth rate, compared with the last previous unvaccinated round.

17 flocks improved, compared to the average over the 5 previous unvaccinated rounds.

The average growth per day was 44.6 grams.

The average growth per day of the last previous unvaccinated rounds was 42.8, an average improvement of 1.8 grams.

The average growth of the previous 5 unvaccinated rounds, averaged over 20 flocks was 42.8.

Total Mortality

Results are shown in table 4.

TABLE 4

|  | Mortality (%) vaccinated | Mortality (%) previously (1 round) | Mortality (%) previously (5 rounds) |
| --- | --- | --- | --- |
| Average 20 farms | 4.2 | 5.2 | 4.4 |

13 flocks out of 20 experienced lower mortality, compared with the last previous unvaccinated round.

12 flocks out of 20 experienced lower mortality, compared to the average mortality over the previous last 5 unvaccinated rounds.

The average mortality was 4.2%.

The average mortality in the last previous unvaccinated rounds was 5.2%, an improvement of 1.0%.

The average mortality in the 5 previous unvaccinated rounds was 4.4. Compared with this figure, the trial rounds improved by 0.2%.

What is claimed is:

1. A method for the protection of broilers from the sub-clinical effects caused by horizontally transmitted CAA, comprising administering a live attenuated CAA vaccine mucosally to the broilers during the first four week after hatch.

2. The method according to claim 1, wherein the vaccine is administered by spray or aerosol, or drinking water.

3. The method according to claim 1, wherein the vaccine is administered to maternally immune broilers.

4. The method according to claim 1, wherein $10^{2.0}$–$10^{6.0}$ TCID$_{50}$ of the live attenuated vaccine is administered to a broiler.

5. A method for preventing production drop syndrome of broilers, comprising mucosally administering a live attenuated chicken anemia agent (CAA) vaccine to the broilers during the first four weeks after hatch, whereby, as compared to unvaccinated broilers, the production index is increased, feed conversion is improved, growth per day is higher, and mortality is lower.

6. The method according to claim 5, wherein the vaccine is administered by spray or aerosol, or drinking water.

7. The method according to claim 5, wherein the vaccine is administered to maternally immune broilers.

8. The method according to claim 5, wherein $10^{2.0}$–$10^{6.0}$ TCID$_{50}$ of the live attenuated vaccine is administered to a broiler.

* * * * *

UNITED STATES PATENT AND TRADEMARK OFFICE
CERTIFICATE OF CORRECTION

PATENT NO.    : 6,270,770 B1
DATED         : August 7, 2001
INVENTOR(S)   : Schrier et al.

It is certified that error appears in the above-identified patent and that said Letters Patent is hereby corrected as shown below:

Claim 1,
Please correct claim 1 by replacing, in the second and third lines, "CAA" with -- chicken anemia agent (CAA) --. Also, in the fourth line, please replace "week" with -- weeks --.

Signed and Sealed this

Fourteenth Day of May, 2002

*Attest:*

JAMES E. ROGAN
*Attesting Officer*  *Director of the United States Patent and Trademark Office*